United States Patent [19]

Cueman et al.

[11] Patent Number: 5,235,858
[45] Date of Patent: Aug. 17, 1993

[54] APPARATUS FOR AIMING TRANSDUCER IN ULTRASONIC GAUGE

[75] Inventors: Michael K. Cueman, Niskayuna; George C. Sogoian, Glenville; John J. Kaehler, Scotia, all of N.Y.; Paul B. Tuck, Wilmington, N.C.

[73] Assignee: General Electric Company, Schenectady, N.Y.

[21] Appl. No.: 908,208

[22] Filed: Jul. 2, 1992

[51] Int. Cl.[5] .......................................... G01N 29/026
[52] U.S. Cl. ...................................... 73/632; 73/629; 73/633
[58] Field of Search .............. 73/632, 633, 629, 866.5, 73/622; 367/173

[56] References Cited

U.S. PATENT DOCUMENTS

| | | | |
|---|---|---|---|
| 3,190,112 | 6/1965 | Beaujard et al. | 73/644 |
| 3,472,065 | 10/1969 | Maxwell | 73/597 |
| 3,672,211 | 6/1972 | Hatch | 73/633 |
| 4,196,607 | 4/1980 | Youtsey et al. | 73/622 |
| 5,074,151 | 12/1991 | John, Jr. et al. | 73/622 |

Primary Examiner—Tom Noland
Assistant Examiner—Nashmiya Ashraf
Attorney, Agent, or Firm—James E. McGinness; James Magee, Jr.

[57] ABSTRACT

An apparatus and method for aiming an ultrasonic transducer is disclosed. A tubular member having an axial bore with the transducer extending therein has an upper section, and a lower section with a threaded outer surface and an inner receiving surface. A ferrule assembly includes a compression nut mating with the threaded surface, and a ferrule biased by the compression nut against the receiving surface to form a waterproof seal with the transducer. A collar having a first annular section is detachably mounted coaxially on the tubular member. The first annular section extending to a second annular section having cut-outs suitable for providing access to manipulate the compression nut. The second annular section extending to a third annular section having a positioning members facing a section of the transducer extending from the tubular member.

6 Claims, 3 Drawing Sheets

APPARATUS FOR AIMING TRANSDUCER IN ULTRASONIC GAUGE

This application is related to copending application Ser. No. 908,207, filed Jul. 2, 1992.

This invention relates to an ultrasonic gauging apparatus, and in particular to an apparatus for aiming the transducer therein.

BACKGROUND OF THE INVENTION

Ultrasonic gauging employs sound waves or mechanical vibrations whose frequency is above the audible range in the frequency spectrum. The sound is produced by a transducer exhibiting piezo electric properties where electrical energy is converted into mechanical vibrations or, conversely, mechanical vibrations are converted into an electrical signal. Thus, the transducer can be used to transmit ultrasonic waves and to detect or receive the waves. The sound produced by the transducer is introduced into the body to be gauged through a liquid couplant such as water or oil, and generally propagates in a fairly well defined beam through the material. The propagation continues until some or all of the sound is reflected by a boundary, for example, the inner wall of a tube.

Specialized techniques have been developed to extend the usefulness of the ultrasonic equipment. One apparatus, known as a bubbler, consists of a semicontained liquid column. The transducer is sealably mounted in one end of the column, and the body being gauged substantially covers the other end. There can be some leakage of couplant where the body covers the column end, and the leakage can be minimized by proper design. The bubbler provides a solid column of water substantially free of air bubbles between the transducer and the body being gauged. A completely free flowing liquid column can be used where the motion or temperature of the body being gauged is excessive.

The pulse-echo technique of ultrasonic gauging employs a short burst of ultrasonic energy known as the initial pulse. It is transmitted into the body by the transducer through the coupling medium. The ultrasonic impulse travels in essentially a straight line until it strikes a reflecting surface such as the oppositely facing tube surface. The ultrasonic reflection of the wave from the surface is governed by well known laws, analogous to the laws of optics. Any of the reflected energy that returns to the transducer is detected as an echo signal, and its amplitude and location in time are related to the thickness of the tubing wall. To measure the wall thickness of a cylindrical body, the pulse-echo ultrasound measurement requires precise alignment and focusing of the ultrasound beam with the body.

For example, ultrasound can be used to measure the wall thickness of a tube by timing the interval between reflections of the sound wave from the inner and outer surfaces of the wall. The transducer must be aimed so that the beam of ultrasonic waves is directed radially to the cylinder axis, herein referred to as the reference axis, and focused at a preselected location within the wall or inner diameter of the tube. Misalignment of the transducer can cause attenuation of the reflected sound waves, and an incorrect measurement of the wall thickness.

One aspect of this invention is to provide an apparatus for aiming a transducer in an ultrasonic gauging apparatus.

BRIEF DESCRIPTION OF THE INVENTION

An apparatus for aiming an ultrasonic transducer is comprised of a cylindrical mounting means having an axial bore with the transducer extending therein. The cylindrical mounting means having an upper section, and a lower section having a threaded outer surface and an inner receiving surface. A ferrule mounting means comprised of a compression nut mating with the threaded surface, and a ferrule biased by the compression nut against the receiving surface to form a waterproof seal with the transducer. A collar means having a first annular section with detachable mounting means is mounted coaxially on the cylindrical mounting means. The first annular section extending to a second annular section having cut-outs suitable for providing access to manipulate the compression nut. The second annular section extending to a third annular section having adjustable positioning means facing a section of the transducer extending from the cylindrical mounting means.

DETAILED DESCRIPTION OF THE INVENTION

Figure 1:
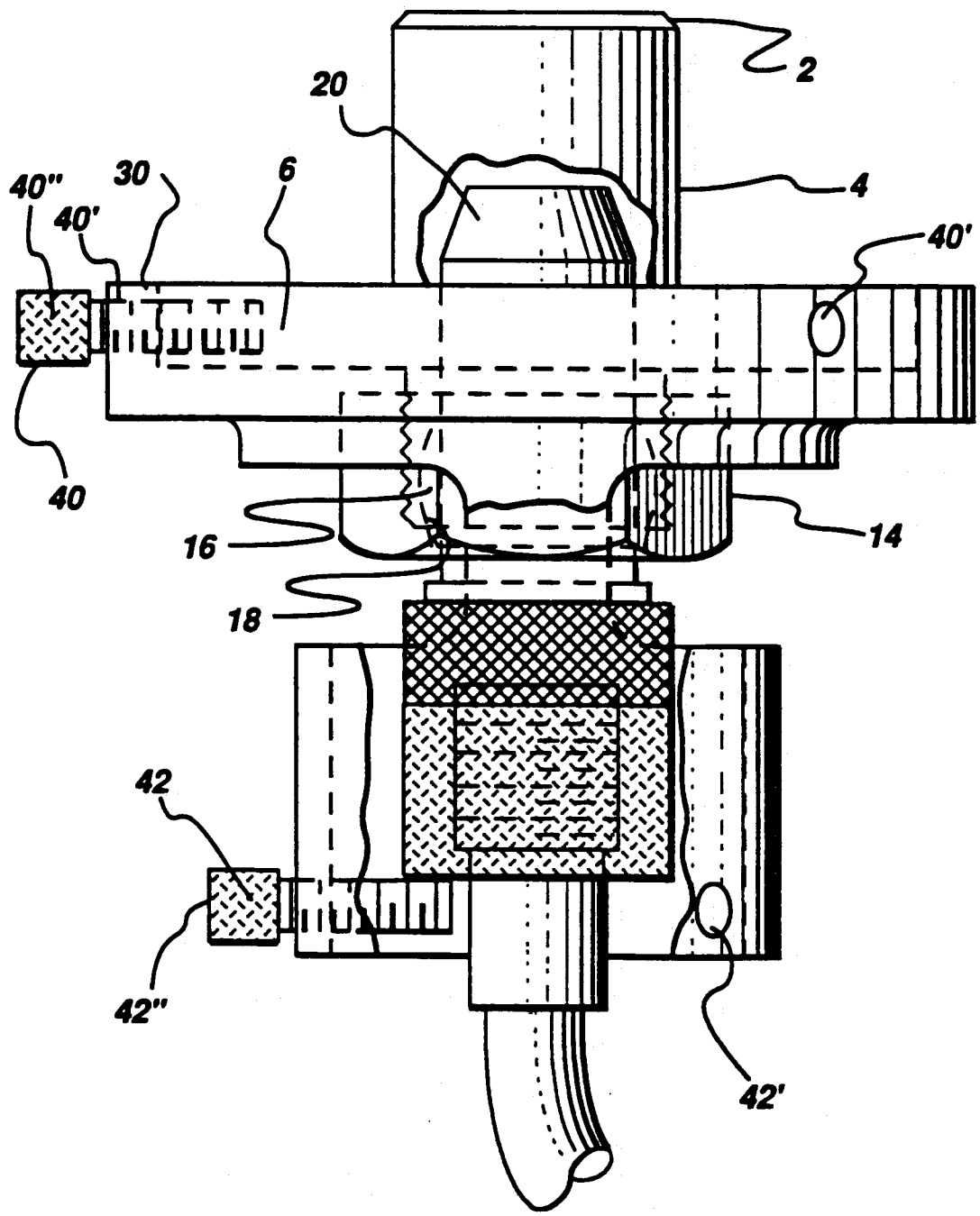
FIG. 1 is a side view of a collar means in FIG. 3 mounted on a cylindrical mounting means in FIG. 2.
Figure 2:
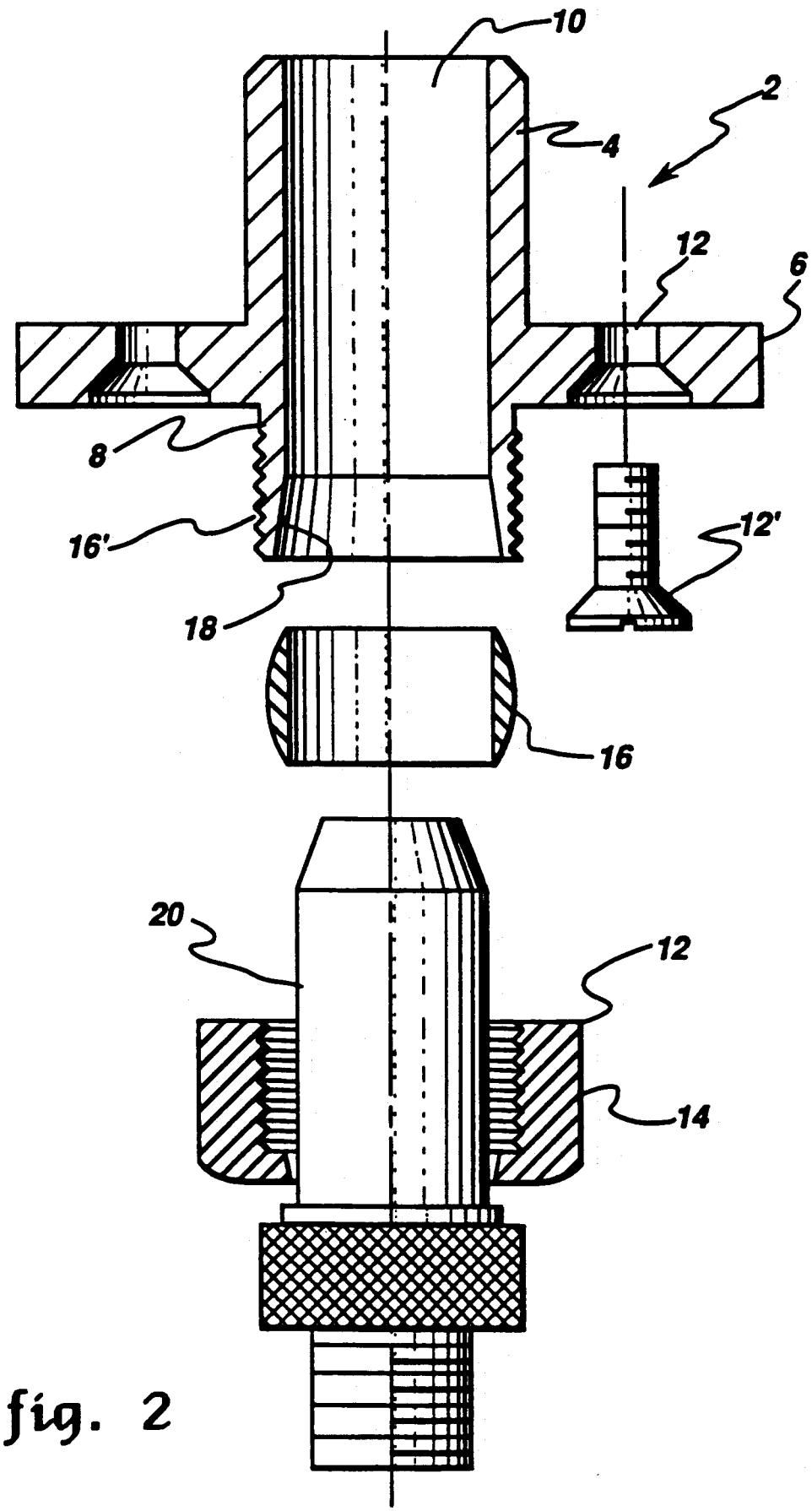
FIG. 2 is an exploded side view of a partial cross-section of the cylindrical mounting means having an ultrasonic transducer positioned therein.

Referring to FIG. 1, an apparatus for aiming an ultrasonic transducer 20 is comprised of a mounting means 2, and a collar means 30 mounted thereon. Referring to FIG. 2, the cylindrical mounting means 2 is comprised of an upper section 4, extending to a lower section 8. The cylindrical mounting means can be mounted on a platform, for example shown in copending application Ser. No. 07,908,207, incorporated herein by reference, suitable for positioning the transducer to ultrasonically gauge bodies. Preferably, the cylindrical mounting means is formed with a mid-flange 6 between the upper and lower sections having at least one bore 12 for conventional fastener 12' attachment on the platform.

The cylindrical mounting means 2 is formed from a rigid corrosion resistant material such as stainless steel, with an axial bore 10 larger than the transducer 20. The lower section 8 extends to a ferrule mounting means 12 comprised of a compression nut 14, and ferrule 16. The compression nut can be formed from a suitable steel, and the ferrule is preferably formed from an electrically insulating material such as nylon. The lower section 8 having a threaded outer surface 16' and an inner receiving surface 18. The compression nut 14 mating with the threaded surface 16' of lower section 8, and biasing ferrule 16 against the receiving surface 18 to form a seal with the ultrasonic transducer 20. Compression nut 14 can be turned to bias ferrule 16 against receiving surface 18, and form a seal between the ferrule mounting means 12 and the transducer 20 fixing the transducer in a preselected orientation.

Figure 3A:
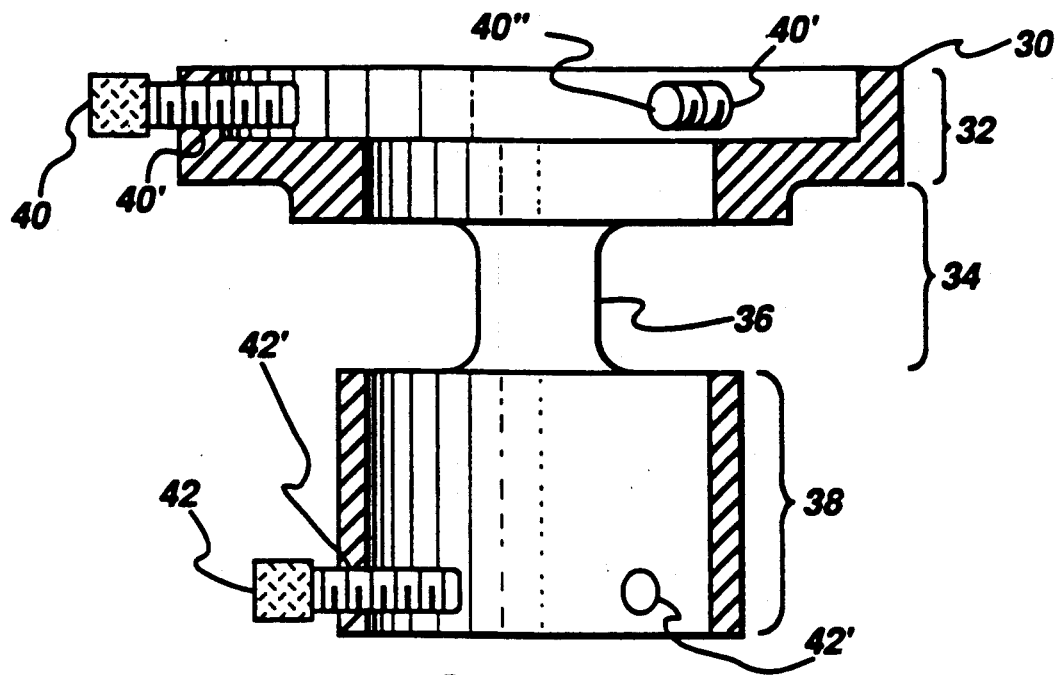
FIGS. 3a and 3b are a side view and top view, respectively, of the collar means.

Referring to FIG. 3a, the collar means 30 is comprised of a first annular section 32 extending to a second annular section 34 having cut-outs 36 formed therein, and second annular section 34 extends to third annular section 38. The inside diameter of first annular section 32 is formed to mate with the outside diameter of the mid-flange 6 of the cylindrical mounting means 2. The inside diameter of second annular section 34, and third annular section 38 are greater than the outside diameter of compression nut 14 so that the collar means 30 can be mounted on, and removed from the cylindrical mounting means 2.

Figure 3B:
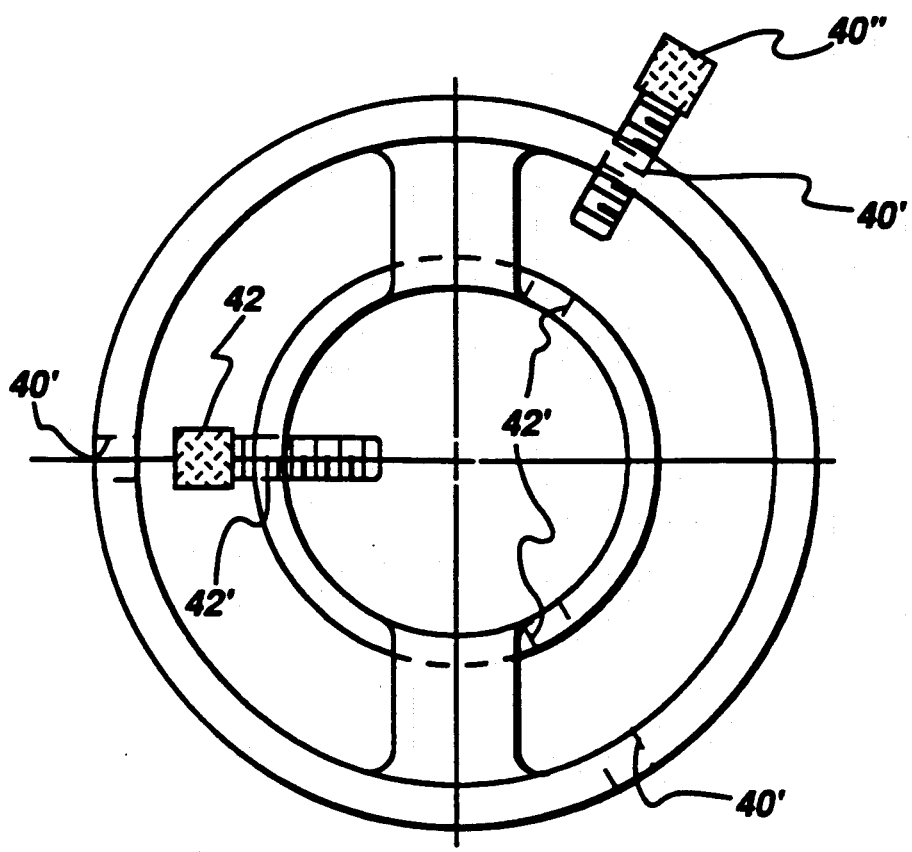

The first annular section 32 has detachable mounting means 40 for mounting the collar means coaxially on the cylindrical mounting means. For example, referring to FIG. 3b, three equally spaced threaded bores 40' are formed in the first annular section. Conventional fasteners 40" mating with the threaded bores can be turned to secure the collar means to the cylindrical mounting means 2. The cutouts 36 in second annular section 34 are formed so that the compression nut 14 can be accessed, and manipulated to tighten or loosen the ferrule 16 between the compression nut 14 and the receiving surface 18. Lower annular section 38 has adjustable positioning means 42 that provide for aiming the transducer 20. For example, three equally spaced threaded bores 42' are formed in lower annular section 38. Conventional fasteners 42" mating with threaded bores 42' are positioned therein.

Referring to FIG. 1, the collar means 30 is co-axially mounted on the cylindrical mounting means 2 by biasing fasteners 40" against the mid-flange 6 of cylindrical mounting means 2. The cut-outs 36 in the second annular section 34 provide access to compression nut 14, which is turned sufficiently to bias ferrule 16 against receiving surface 18 so that the ferrule is snug but allows movement of transducer 20. The fasteners 42" are turned to contact the transducer 20, and manipulated to aim the transducer in a preselected orientation. For example, the transducer can be aimed so that the ultrasonic wave from the transducer is radial to the axis of a cylindrical body positioned above the cylindrical mounting means. The transducer can be translated along the axis of the cylindrical mounting means 2 to focus the ultrasonic beam from the transducer at a preselected location, for example, within the wall thickness of the cylindrical body. The aiming and focusing steps can be repeated in a series of iterative steps to minimize attenuation of the ultrasonic waves in the body being gauged, and provide the desired reflection ultrasonic wave intervals for gauging the wall thickness of the body. The compression nut 14 is turned to bias ferrule 16 against receiving surface 18, and form a seal with transducer 20 fixing the transducer in the desired orientation. The collar means 30 can be removed from the cylindrical mounting means 2 by loosening fasteners 40", and sliding the collar off the cylindrical mounting means.

What is claimed is:

1. An apparatus for aiming an ultrasonic transducer comprising:
   a tubular member having the transducer extending therein, the tubular member having an upper section, and a lower section having a threaded outer surface and an inner receiving surface, a ferrule mounting means comprised of a compression nut mating with the threaded surface, and a ferrule biased by the compression nut against the receiving surface to form a waterproof seal with the transducer, and
   a collar having a first annular section detachably mounted coaxially on the tubular member, the first annular section extending to a second annular section having cut-outs suitable for providing access to manipulate the compression nut, the second annular section extending to a third annular section having adjustable positioning members facing a section of the transducer extending from the tubular member.

2. An apparatus according to claim 1 wherein the tubular member has a mid-flange between the upper and lower sections, and the collar is detachably mounted on the mid-flange.

3. An apparatus according to claim 2 wherein the collar is detachably mounted by three bolts extending through mating threaded bores equally spaced around a circumference of the first annular section, and the adjustable positioning members ar three bolts extending through mating threaded bores equally spaced around a circumference of the third annular section.

4. A method for aiming a transducer, comprising:
   mounting the transducer in a tubular member having an upper section, and a lower section having a threaded outer surface and an inner receiving surface, a ferrule mounting means comprised of a compression nut mating with the threaded surface, and a ferrule in contact with the transducer biased by the compression nut against the receiving surface so that the transducer can be moved,
   mounting a collar having a first annular section detachably mounted coaxially on the tubular member, the first annular section extending to a second annular section having cut-outs suitable for providing access to manipulate the compression nut, the second annular section extending to a third annular section having adjustable positioning members facing a section of the transducer extending from the tubular member,
   manipulating the adjustable positioning members to aim the transducer, and
   turning the compression nut to bias the ferrule against the receiving surface to form a seal with the transducer.

5. A method according to claim 4 wherein the tubular member has a mid-flange between the upper and lower sections, and the collar is detachably mounted on the mid-flange.

6. A method according to claim 4 comprising translating the transducer along an axis of the tubular member to focus an ultrasonic beam from the transducer at a preselected location, before the step of turning the compression nut.

* * * * *